United States Patent
Hoffman

(10) Patent No.: US 7,837,641 B2
(45) Date of Patent: Nov. 23, 2010

(54) HAND ORTHOSIS

(76) Inventor: Michael A. Hoffman, 2659 Sanitarium Rd., Clifton Springs, NY (US) 14432

( * ) Notice: Subject to any disclaimer, the term of this patent is extended or adjusted under 35 U.S.C. 154(b) by 260 days.

(21) Appl. No.: 12/120,917

(22) Filed: May 15, 2008

(65) Prior Publication Data

US 2009/0287123 A1   Nov. 19, 2009

(51) Int. Cl.
*A61F 5/00* (2006.01)
(52) U.S. Cl. .......................... 602/20; 602/21
(58) Field of Classification Search ............ 602/5, 602/16, 20–23, 26, 27; 128/882; 2/16, 18–20, 2/161.1, 161.2
See application file for complete search history.

(56) References Cited

U.S. PATENT DOCUMENTS

| | | | |
|---|---|---|---|
| 2,318,864 A | 5/1943 | Jackson | |
| 2,566,215 A | 8/1951 | Croix | |
| 3,036,312 A | 5/1962 | Larsen et al. | |
| 3,295,518 A | 1/1967 | Hazlewood et al. | |
| 3,724,456 A | 4/1973 | Waxman | |
| 3,967,321 A | 7/1976 | Ryan et al. | |
| 4,009,496 A | 3/1977 | Allen, III | |
| 4,447,912 A | 5/1984 | Morrow | |
| 4,716,892 A | 1/1988 | Brunswick | |
| 4,719,063 A | 1/1988 | White | |
| 4,782,825 A | 11/1988 | Lonardo | |
| 5,205,812 A | 4/1993 | Wasserman | |
| 5,358,471 A | 10/1994 | Klotz | |
| 5,383,827 A | 1/1995 | Stern | |
| 5,466,202 A | 11/1995 | Stern | |
| 5,593,369 A | 1/1997 | Stern | |
| 5,637,078 A | 6/1997 | Varn | |
| 5,672,151 A | 9/1997 | Calderon-Garciduenas | |
| 5,733,249 A | 3/1998 | Katzin et al. | |
| 5,766,142 A * | 6/1998 | Hess | 602/22 |
| 5,772,620 A | 6/1998 | Szlema et al. | |
| 5,782,784 A | 7/1998 | Wassermann | |
| 5,865,783 A * | 2/1999 | Klimoski | 602/64 |
| 6,120,471 A | 9/2000 | Varn | |
| 6,165,148 A | 12/2000 | Carr-Stock | |
| 6,238,358 B1 * | 5/2001 | Philot et al. | 602/5 |
| 6,261,253 B1 | 7/2001 | Katzin | |
| 6,692,453 B2 | 2/2004 | Wolfe | |

* cited by examiner

Primary Examiner—Michael A. Brown
(74) Attorney, Agent, or Firm—Brooks Kushman P.C.

(57) ABSTRACT

A hand orthosis assembly comprising a substantially rigid splint member having an inner wrist portion configured to receive a person's inner wrist and an arcuate palm portion extending from the wrist portion to receive the person's cupped hand. The arcuate palm portion may defining a cavity adapted to releasably retain a tool or recreational device, or an interchangeable insert releasably retained within the cavity, for generally gripping a tool or recreational device for functional use. The assembly may additionally include two or more protrusions extending from an outer perimeter of the arcuate portion for maintaining the persons' fingers in generally correct alignment. The assembly may also include a hook portion extending from the arcuate palm portion, having an assisting member extending therefrom for handling objects. The assisting member may be magnetic or affixed to magnetic material.

8 Claims, 5 Drawing Sheets

HAND ORTHOSIS

BACKGROUND OF THE INVENTION

1. Field of the Invention

Embodiments of the present invention relate generally to therapeutic rehabilitation devices and more specifically to hand orthosis devices.

2. Background Art

U.S. Pat. No. 5,766,142 describes a hand orthosis that has a base member, which supports the palm and fingers of a patient. The base member has a cover which extends at least over the finger support area. A plurality of spaced parallel forwardly extending finger separators extend outwardly from the cover to form a plurality of finger channels therebetween. A flexible strap is secured to the base member and extends laterally across the separators and the channels. The cover and the separators are composed of a washable perspiration absorbing material.

U.S. Pat. No. 6,120,471 provides a dorsal resting hand orthosis, which has a substantially rigid splint member. The splint member has a wrist portion adapted to fit and receive the dorsal side of a patient's wrist. The splint also includes two lateral supports connected to a finger portion. The lateral supports are wide enough to allow a patient's knuckles to slide easily in between. The finger portion is attached to a thumb portion and together are adapted to receive the cupped hand of a patient who has their fingers juxtapositioned with the thumb in space gripping position opposite of the patient's fingers. A resilient liner extends along the inner surface of the splint and is easily removable. Straps are secured to the liner to secure the splint to the patient's forearm, wrist, fingers, and thumb.

SUMMARY OF THE INVENTION

One embodiment of the present invention includes hand orthosis device. In this embodiment, the hand orthosis device includes a substantially rigid splint member with an inner wrist portion configured to receive a person's inner wrist. The hand orthosis device also includes an arcuate palm portion extending from the wrist portion to receive the person's cupped hand. The arcuate palm portion may define a cavity adapted to receive and grip a tool or recreational device for functional operation by the person. Two or more protrusions may extend from an outer perimeter of the arcuate portion for maintaining the person's fingers in generally correct alignment over the arcuate portion. A substantially rigid hook portion may extend from the arcuate palm portion and include at least one substantially rigid assisting member extending therefrom for handling objects.

In other embodiments, the cavity defined by the arcuate palm portion may be configured to receive a removable insert for changing the shape or diameter of the cavity. The substantially rigid assisting member(s) may include one or more substantially magnetic members for manipulating ferrous materials.

One or more strap elements may be provided for fastening at least one of the person's wrist or arm to the hand orthosis. The splint member, arcuate palm portion, and hook portion may be of unitary construction, and may comprise a plurality of different materials, including steel, aluminum, plastic, fiberglass, semi-rigid rubber, etc.

In another embodiment, the arcuate palm portion may comprise a deformable material which may be compressed and released by the person to grip and release the tool or recreational device within the cavity.

This summary is provided without limitation on the scope of the present invention. Other aspects and embodiments of the present invention will become readily apparent from the following detailed description of the preferred embodiments.

DETAILED DESCRIPTION OF THE PREFERRED EMBODIMENT(S)

Figure 1:
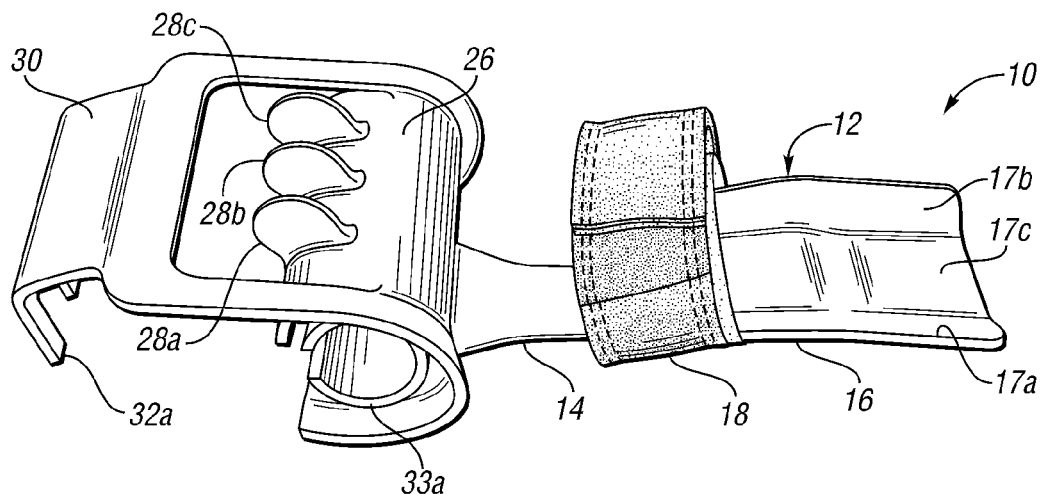
FIG. 1 shows a perspective view of a hand orthosis in accordance with at least one embodiment of the present invention.
Figure 2:
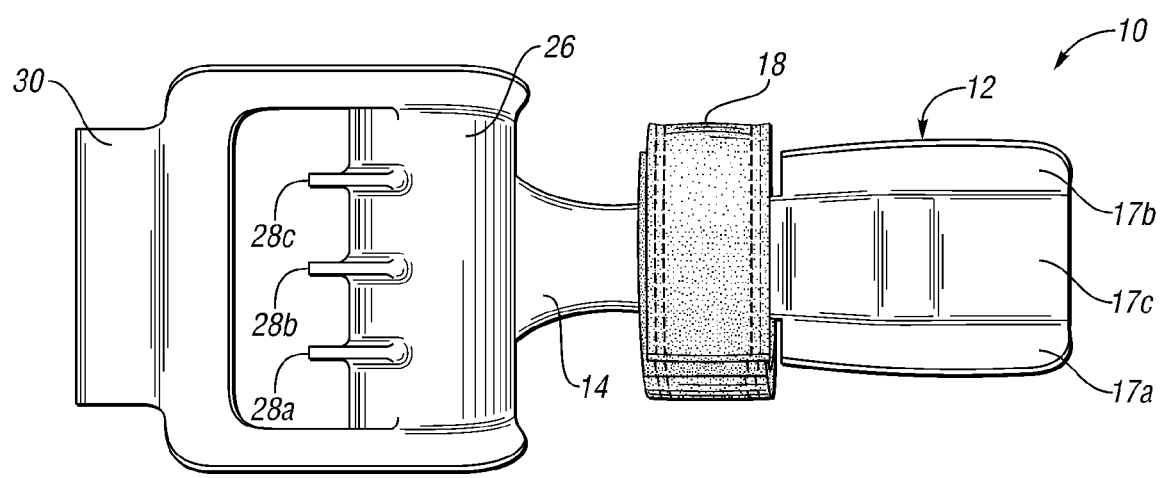
FIG. 2 shows a top plan view of the hand orthosis shown in FIG. 1, in which the wrist strap portions are attached.

The following described embodiments are not presented as limitations of the present invention, but as examples enabling those of skill in the art to make and use what is more generally recited in the appended claims. Those of skill in the art will appreciate, based on the written description as a whole, that other embodiments may exist within the scope of the present invention.

Referring generally to FIGS. 1-4, a preferred embodiment of a hand orthosis 10 is shown. The orthosis 10 may include a substantially rigid splint member 12 which may include inner wrist portion 14 and arm support portion 16. Arm support portion 16 includes a center portion 17c and flanges 17a and 17b, which are upwardly inclined relative to the center portion 17c to accommodate the shape of a user's forearm. Of course, one skilled in the art will recognize that the geometry and material used to define the splint 12 may vary depending on the particular user or implementation thereof. For example, the splint member may be made of rigid or semi-rigid plastic, aluminum, or leather. In another variation, weight may be reduced without sacrificing necessary strength and stiffness by defining a rib frame configuration for the splint 12. Padding or abrasive material (not shown) may also be applied to splint 12 for comfort and/or support.

Figure 3:
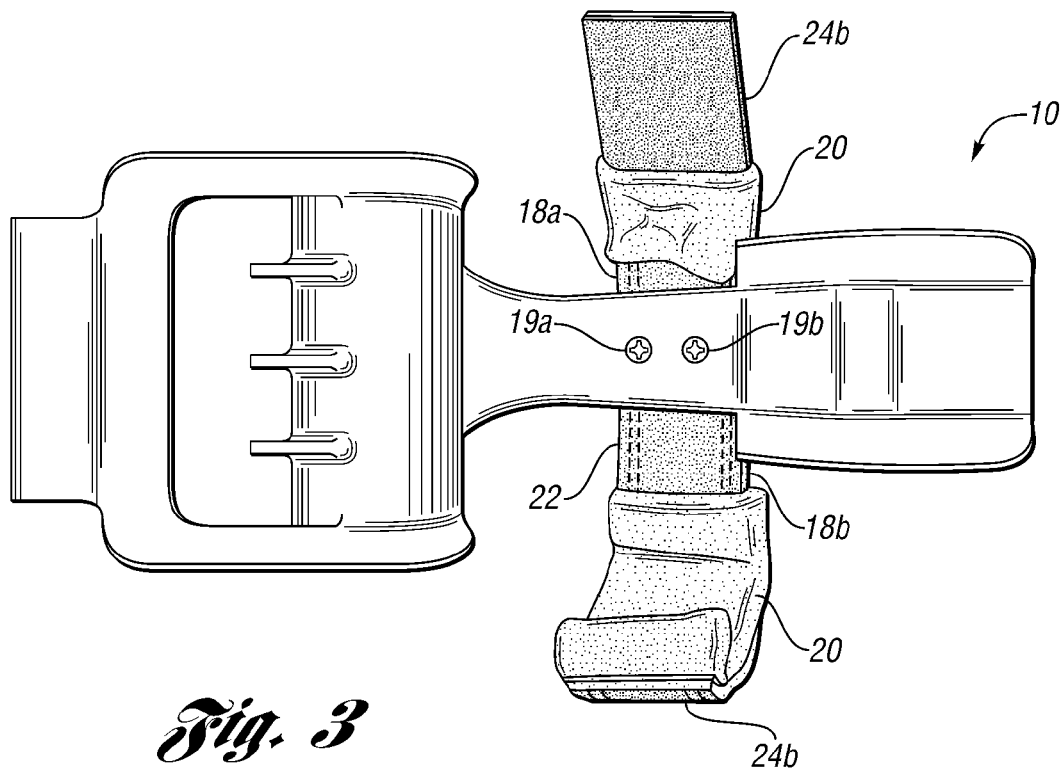
FIG. 3 shows a top plan view of the hand orthosis shown in FIG. 1, in which the wrist strap portions are detached.
Figure 5:
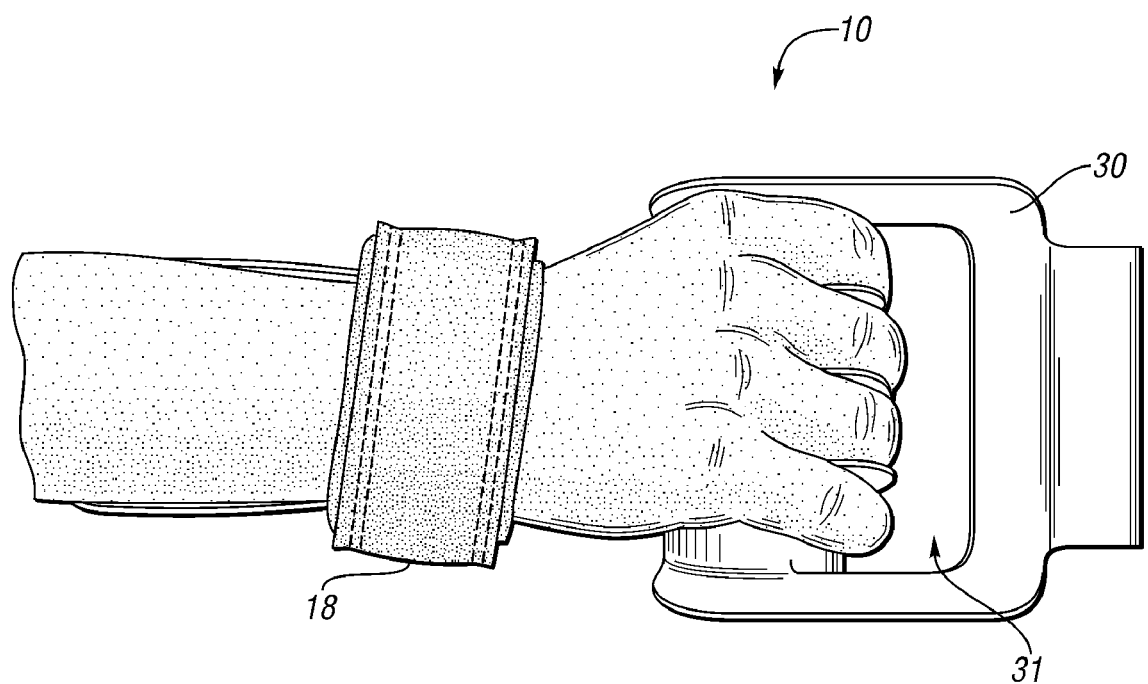
FIG. 5 shows a perspective view of a user gripping the hand orthosis depicted in FIGS. 1-4.
Figure 6:
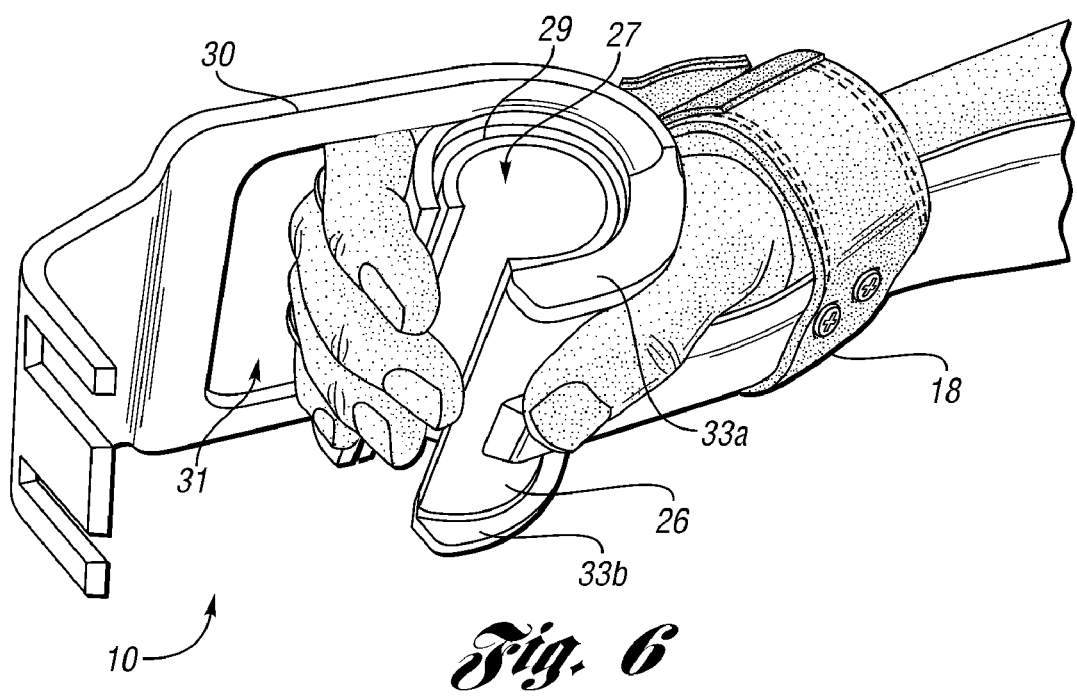
FIG. 6 shows a top plan view of a user gripping the hand orthosis shown in FIGS. 1-4.
Figure 8:
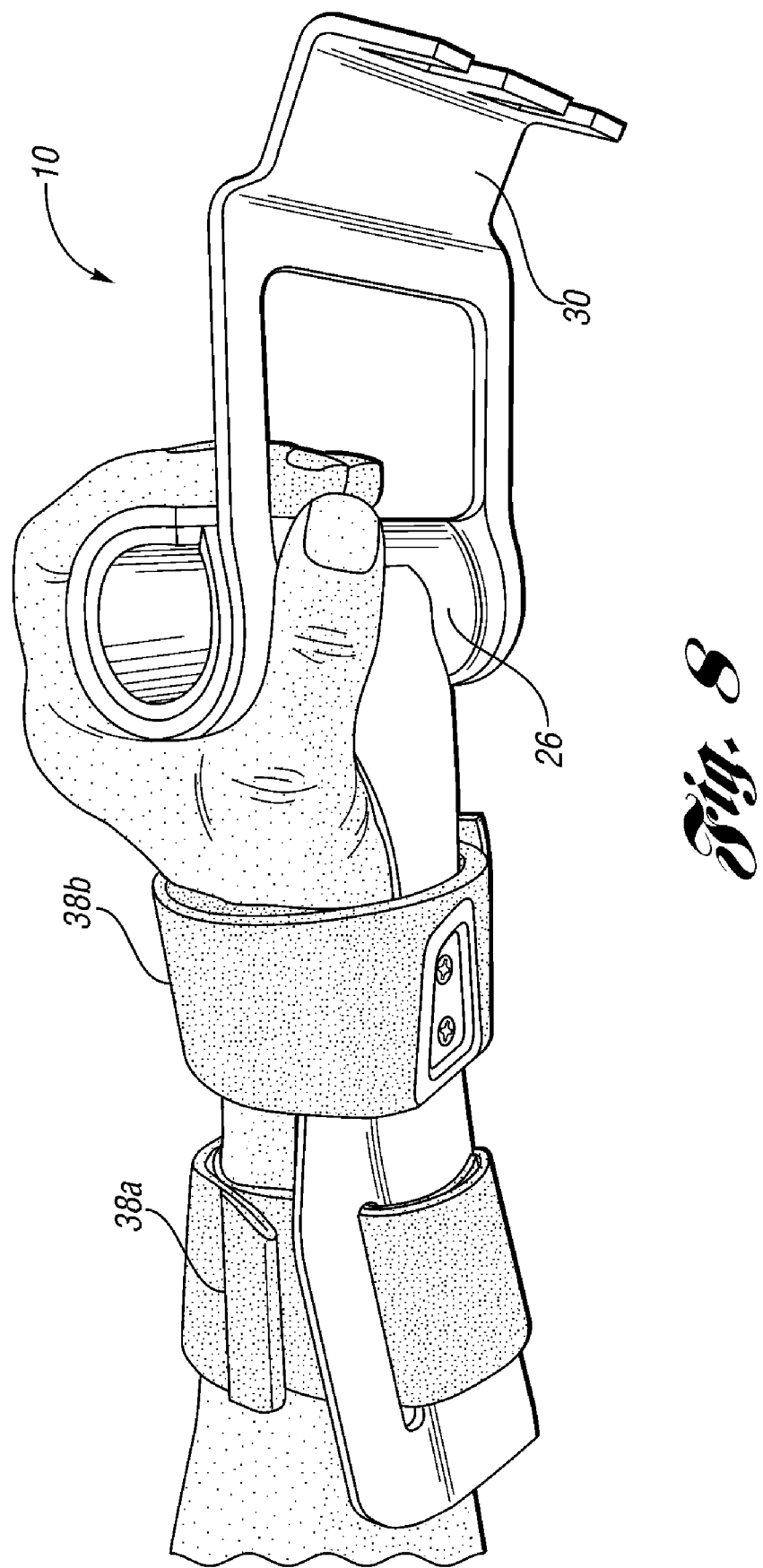
FIG. 8 shows a perspective view of a user gripping a hand orthosis in accordance with an embodiment of the invention.

A strap 18 may be affixed to the splint 12. In the illustrated embodiment, two screws 19 may be used. In implementation, any suitable fastener can be used. The strap 18 secures the user's wrist to the orthosis 10. This is best shown in FIGS. 5-6. Referring to FIG. 3, strap 18 may include an inner cushioning layer 20 affixed to a deformably rigid layer 22. A hook and loop fastener 24 may be adjoined to respective strap portions 18a and 18b to releasably affix the two portions. The cushioning layer 20 is preferably soft, and is meant to provide comfort to the user's arm. It will be appreciated by one skilled in the art that the strap 18, and its associated elements (e.g., the cushioning layer), may be configured in a variety of ways and is not meant to be limiting to the scope of the present invention. For example, a hook-and-loop fastener strap may be used, or multiple straps may be used, as shown in FIG. 8. In an alternative embodiment, semi-rigid plastic extending from the splint 12 and extending cylindrically around the location of the user's forearm may be used to sufficiently secure the orthosis.

With reference to FIGS. 1 and 6, an arcuate palm portion 26 may extend from the wrist portion 14 and is configured to receive a person's cupped hand. In the embodiment shown, three protrusions, 28a-c, may extend outwardly from the wrist portion 26. These protrusions may be configured to support the person's fingers or preclude excessive lateral finger movement. Protrusions 28 may also be provided at the ends of the arcuate portion 26 for retaining or otherwise limiting excessive lateral movement of the user's thumb. The protrusions may be substantially flange-like as illustrated, or less pronounced as ridges extending from the outer perimeter of the arcuate portion 26.

As shown in FIG. 6, the user's fingers and thumb generally form a "C-shape" about the arcuate portion 26. The person's hand, wrist and fingers may be confined by the geometry of the orthosis 10. In this manner, the orthosis 10 holds a user's wrist, hands, and finger in proper alignment.

A patient wearing an embodiment of the hand orthosis may wish to perform a variety of tasks while wearing the device, such as, but not limited to, exercising, performing housekeeping tasks, yard work, sports activities, etc. Embodiments of the present invention may include features that enable a user to make functional use of his or her confined hand.

Figure 4:
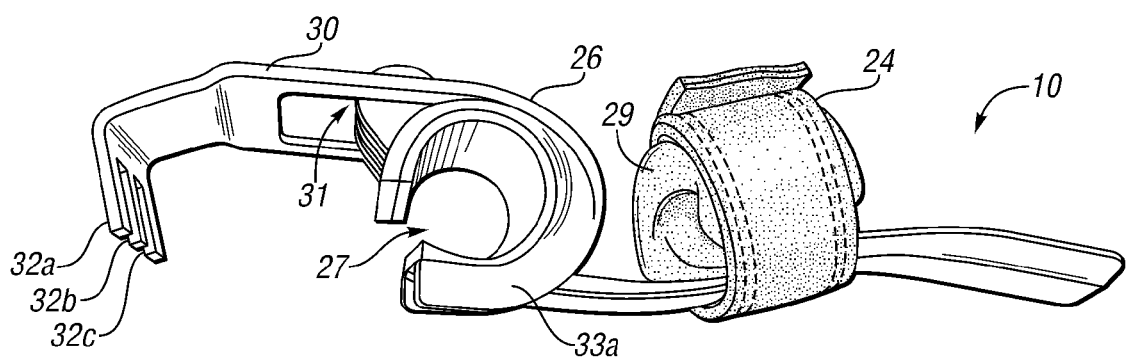
FIG. 4 shows a side elevational view of the hand orthosis illustrated in FIG. 1.
Figure 7A:
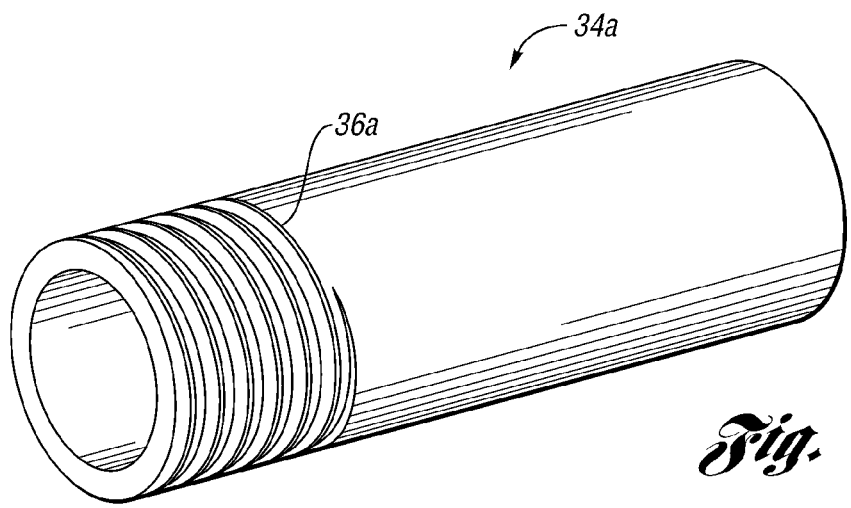
FIGS. 7A-7C show inserts that may be used in accordance with hand orthosis embodiments of the present invention.
Figure 7B:
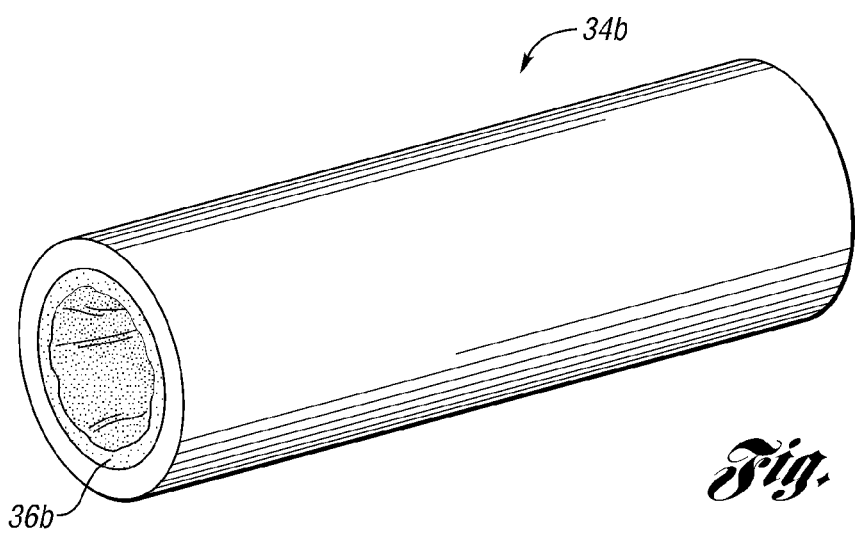
Figure 7C:
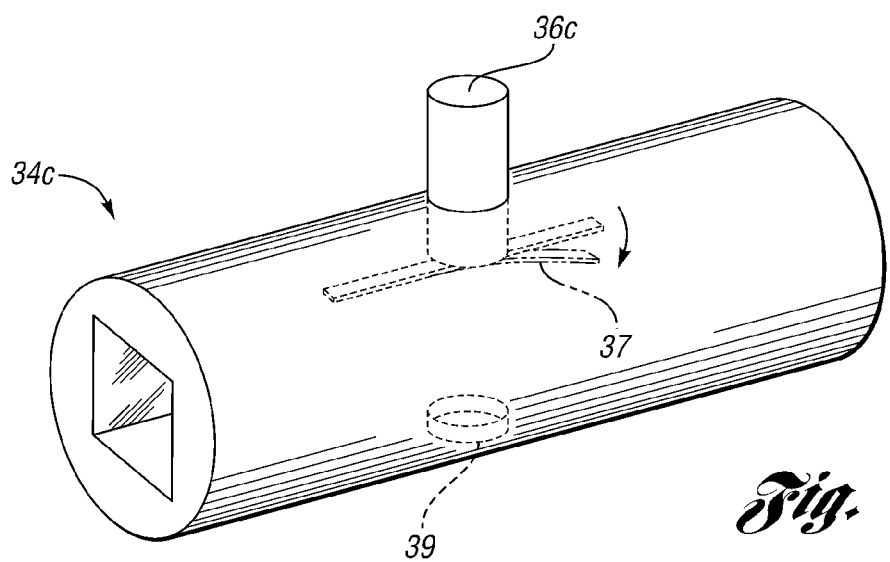

Referring to FIGS. 4 and 6, the arcuate palm portion 26 may define a cavity 27. In the shown embodiment, the cavity 27 may extend axially along the length of the arcuate portion 26 and may have an axially extending opening approximately ¾" in width. In alternative embodiments, other diameters may be utilized, and the cavity may be closed on one end. As illustrated in FIG. 7, a plurality of interchangeable inserts 34a-c may be provided allowing a user, or physical therapist, to change the diameter, geometry or general configuration of cavity 27. The inserts may be secured to cavity 27 by threading 36a or spring latch 36c. As shown in FIG. 7B, inserts 35 may have an inner cushion layer 36b therein for gripping objects. One of skill in the art will appreciate from this disclosure that other fastening or securing techniques may be utilized.

The configuration of the cavity 27 enables the user to hold objects via the orthosis 10. For example, a user can hold the handle of a tool; such as a rake, a broom, a shovel, or the like; in effect, providing for its use. Additionally, the user can grip recreational objects, such as a pool cue, ski pole, or exercise equipment. The preceding is meant neither to enumerate the applications of the present invention, nor exhaustively demonstrate the functionality of the shown embodiment.

As illustrated in FIGS. 4 and 6, an inner gripping layer 29 may be affixed to the inner surface of the cavity 27. The gripping layer 29 provides for a frictionally releasable grip and can assist the user by preventing a "gripped" object from slipping axially along the cavity. In an alternative embodiment, the arcuate portion 26 may comprise a semi-rigid deformable material so the user can exert a compressive force on the arcuate portion 26 with his or her hand and/or fingers, effectively increasing the frictional force between the arcuate portion 26 and a gripped object.

As best shown in FIGS. 4-6, one or more substantially rigid hook portions 30 extend from the palm portion 26. A cavity 31 may be configured to allow a patient to remove his or her hand and fingers from the arcuate portion 26 of the orthosis device 10. Substantially rigid, spaced-apart assisting members, generally 32, may extend from the hook portion 30 in any useful direction. Assisting member 32b may be substantially magnetic, whereas members 32a and 32c may be relatively non-magnetic. One skilled in the art will understand that the hook portion 30 may extend from the palm portion 26 via any suitable configuration. For example, in another embodiment of the orthosis 10 (shown in FIG. 8), the hook portion 30 extends from the lower part of the palm portion 26.

The assisting members 32 enable the user to actuate objects using his or her effected hand. For example, a user can push, pull, or lift objects using one or more of the members 32 of the orthosis 10. The assisting members 26, in accordance with an embodiment of the present invention, may further enable a user to manipulate and actuate smaller objects.

The substantially magnetic assisting member(s) 32b and relatively non-magnetic members 32a,32c have a multitude of functional uses for a patient with an effected hand. For example, the members 32, and conceivably other features of the orthosis 10, can enable the user to use his or her effected hand to support relatively small objects for manipulation or actuation by the non-effected hand. As an example, a user can support a metal fastener, such as a nail, with the magnetic assisting member 32b and use his or her non-effected to hammer the nail. Other applications of the assisting members 32 will become apparent to one skilled in the art.

As shown, the orthosis 10 is largely formed of a one-piece construction. A skilled artisan will readily recognize that the orthosis may be formed from multiple pieces which are fastened to one another using a variety of suitable fasteners. For example, the palm portion 26 and the hook portion 30 could comprise a single piece which is secured to the splint via a fastener, such as a bracket. Hook portion 30 may be releasably attached to palm portion 26, for example, by a fastener. Clearly, a number of suitable configurations, constructions, and materials may be used in accordance with the present invention; the embodiment shown and described is not meant to be limiting in this sense.

As described, traditional orthoses may assist in holding a patient's effected wrist and hand in correct alignment. However, such orthoses often preclude a patient from functionally using his or her effected hand. Embodiments described above provide an orthosis with function-enabling features that allow a patient to perform a multitude of tasks more effectively with his or her effected hand.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A hand orthosis comprising:
 a substantially rigid splint member having an inner wrist portion configured to receive a person's inner wrist;
 an arcuate palm portion extending from the wrist portion to receive the person's cupped hand, the arcuate palm portion defining a cavity adapted to receive a tool or recreational device;
 two or more protrusions extending from an outer perimeter of the arcuate portion for maintaining the person's fingers in generally correct alignment over the arcuate portion; and
 a substantially rigid hook portion extending from the arcuate palm portion, the hook portion having at least one substantially rigid assisting member extending therefrom for handling objects.

2. The orthosis of claim 1 wherein the cavity is generally cylindrical.

3. The orthosis of claim 2 wherein the cavity is configured to receive a removable insert for changing the shape or diameter of the cavity.

4. The orthosis of claim 1 wherein the substantially rigid assisting member includes one or more substantially magnetic members.

5. The orthosis of claim 1 wherein one or more of the protrusions comprise flanges extending perpendicularly from the arcuate palm portion.

6. The orthosis of claim 1 comprising one or more strap elements, each strap element adapted to fasten at least one of the person's wrist or arm to the hand orthosis.

7. The orthosis of claim 1 wherein the splint member, arcuate palm portion, and hook portion are of one-piece construction.

8. The orthosis of claim 1 wherein the arcuate palm portion comprises a deformable material which may be compressed and released by the person to grip and release the tool or recreational device within the cavity.

* * * * *